United States Patent

Wagner et al.

[11] Patent Number: 6,099,311
[45] Date of Patent: Aug. 8, 2000

[54] ABUTMENT DELIVERY SYSTEM

[75] Inventors: William R. Wagner, Escondido; Jeffrey A. Bassett, Vista, both of Calif.

[73] Assignee: Sulzer Calcitek Inc., Carlsbad, Calif.

[21] Appl. No.: 09/362,620

[22] Filed: Jul. 28, 1999

[51] Int. Cl.[7] .................................................. A01C 3/00
[52] U.S. Cl. ............................................. 433/163; 81/436
[58] Field of Search .................................... 433/163, 141; 606/104; 81/44, 438, 450, 436

[56] References Cited

U.S. PATENT DOCUMENTS

| | | | |
|---|---|---|---|
| 1,227,391 | 5/1917 | Cooper | 81/436 |
| 4,380,942 | 4/1983 | Fenton | 81/436 |
| 4,465,463 | 8/1984 | H:son Olde | 433/141 |
| 4,995,810 | 2/1991 | Soderberg | 433/141 |
| 5,105,690 | 4/1992 | Lazzara et al. | 81/436 |
| 5,437,550 | 8/1995 | Beaty et al. | 433/141 |
| 5,690,489 | 11/1997 | Carchidi | 433/141 |
| 5,829,324 | 11/1998 | Secor | 81/436 |
| 5,906,146 | 5/1999 | Arlen | 81/436 |

*Primary Examiner*—Todd E. Manahan
*Attorney, Agent, or Firm*—Philip S. Lyren; Kenneth S. Barrow

[57] ABSTRACT

A device for retaining and delivering dental implant components includes a retainer-delivery member which may be pivotally attached to a handle member and selectively detached therefrom. The retainer-delivery member has a plurality of multi-sized stepped down portions for hands-off insertion into, and frictional engagement with various dental implant components. The retainer-delivery member can retain one or more of the components for delivery to the implant site and can be manipulated for initial connection to the implant.

35 Claims, 8 Drawing Sheets

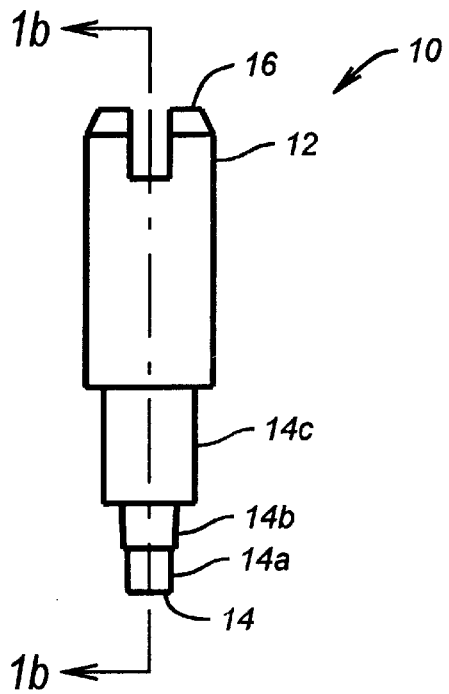
FIG. 1a
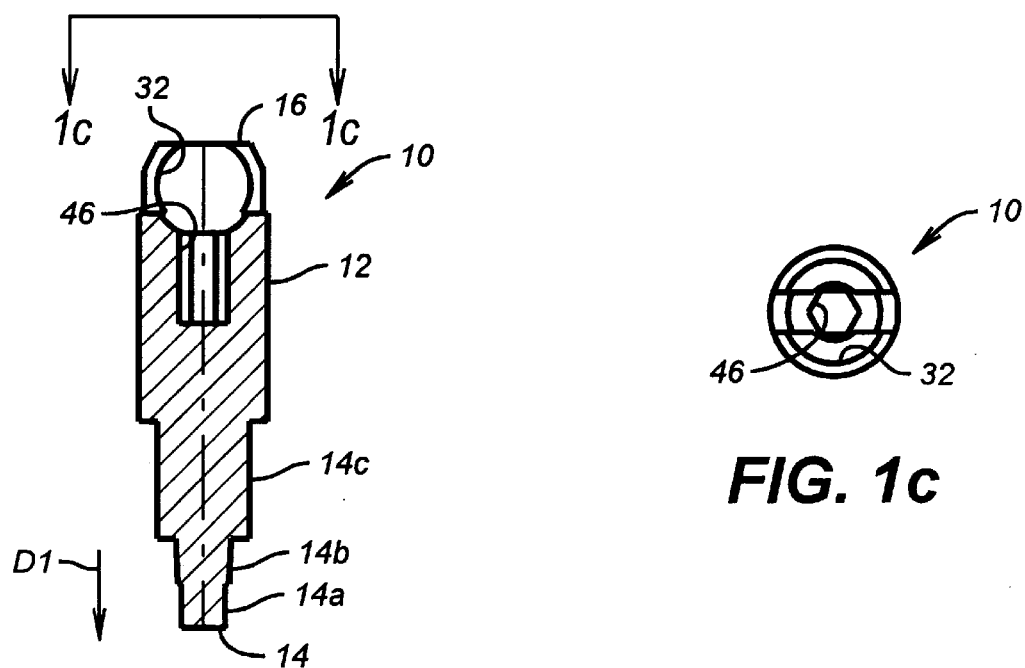
FIG. 1b
FIG. 1c

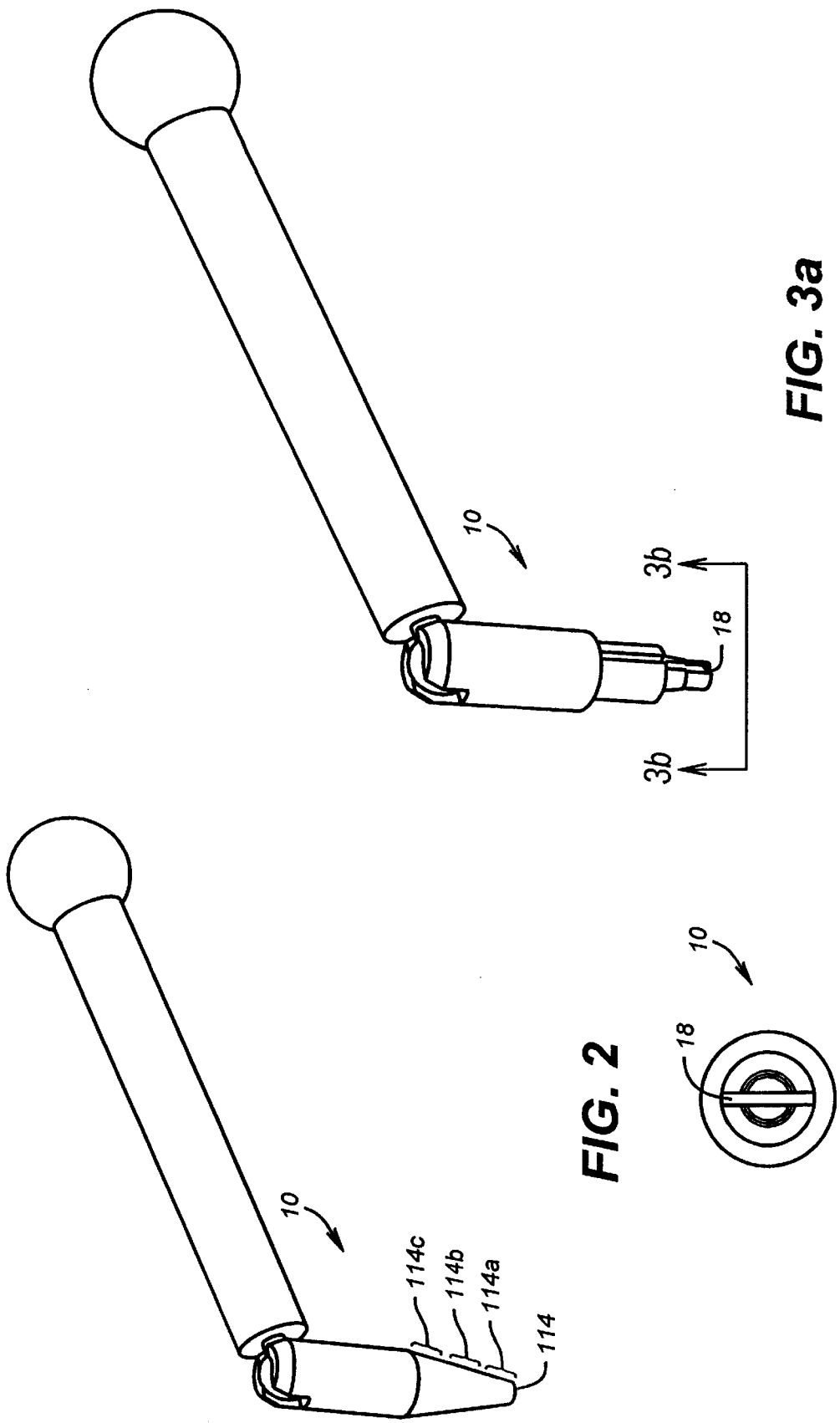

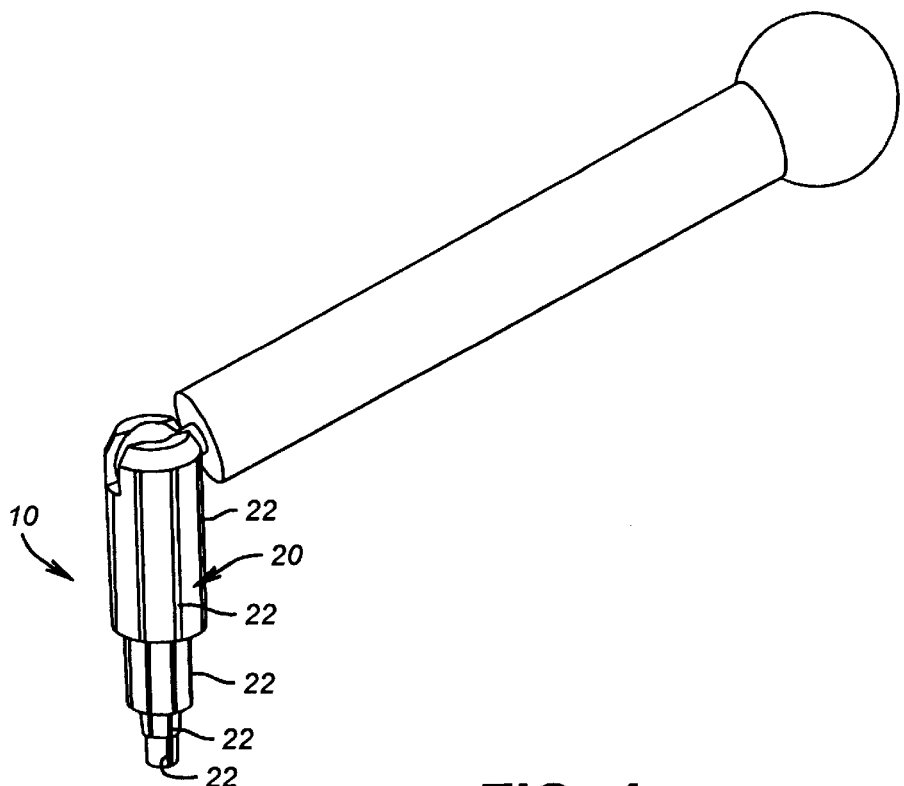
FIG. 4
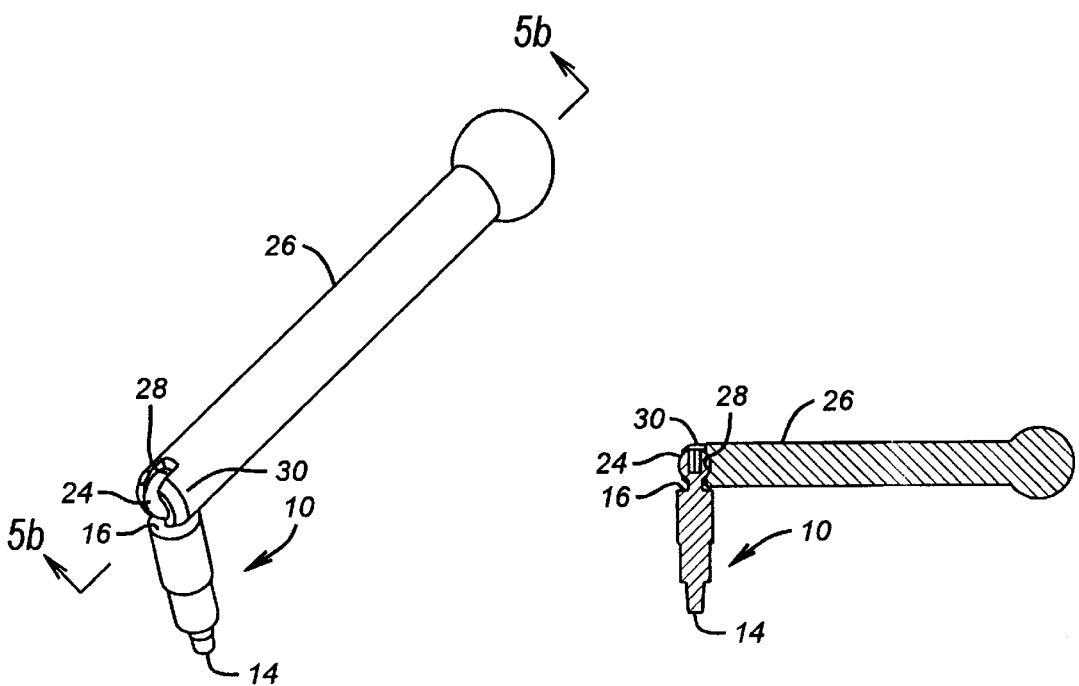
FIG. 5a
FIG. 5b

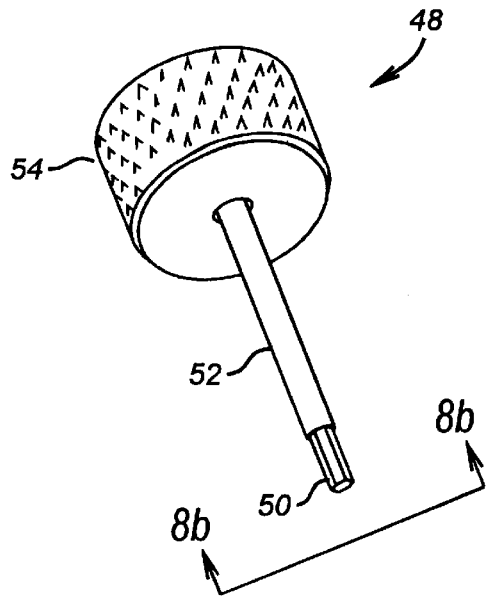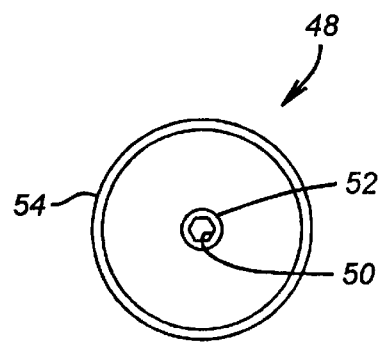
FIG. 8a
FIG. 8b
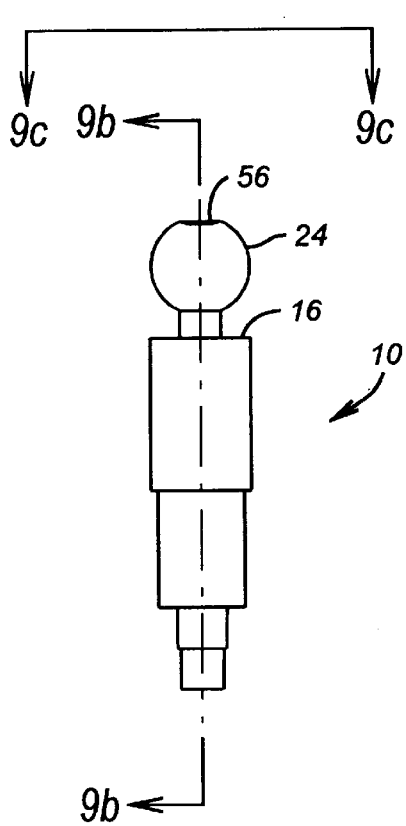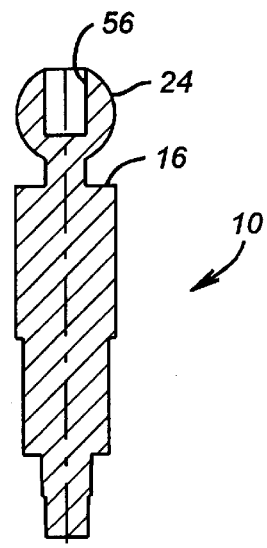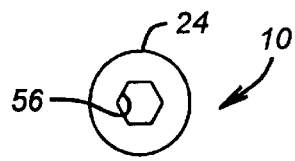
FIG. 9a
FIG. 9b
FIG. 9c

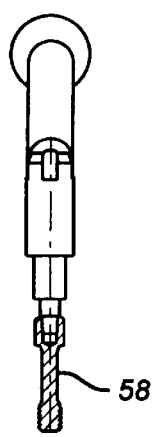 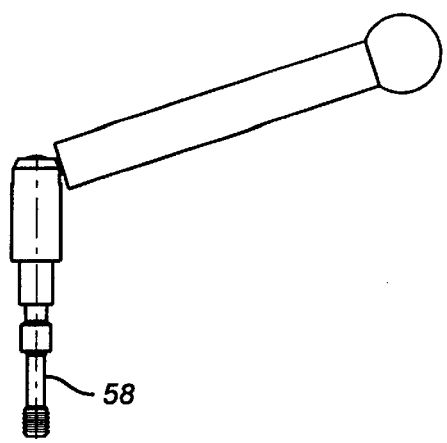
FIG. 10a  FIG. 10b
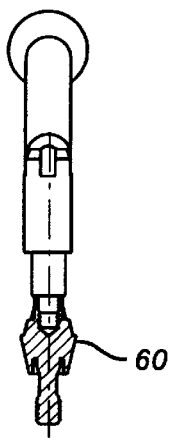 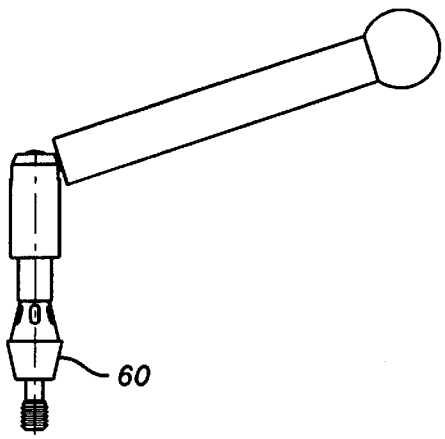
FIG. 11a  FIG. 11b
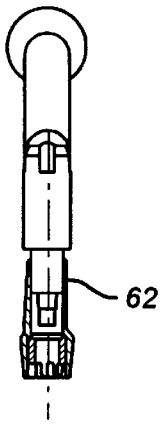 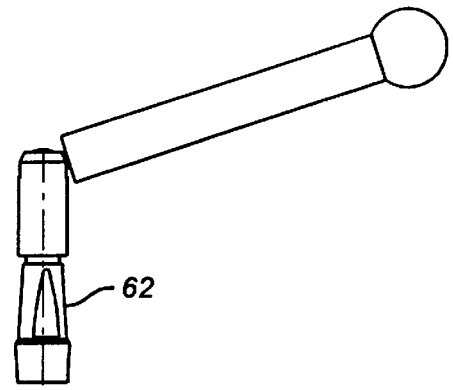
FIG. 12a  FIG. 12b

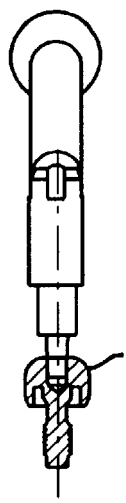 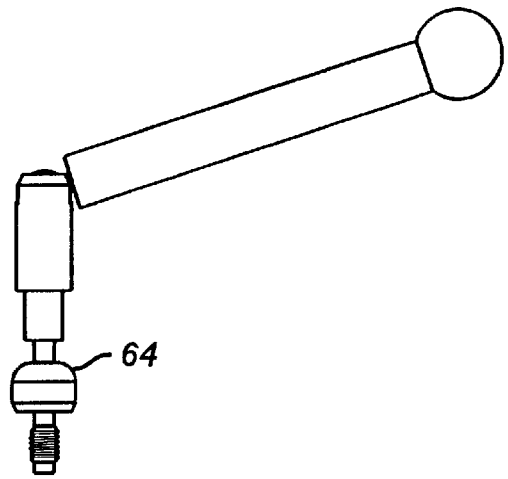
FIG. 13a  FIG. 13b
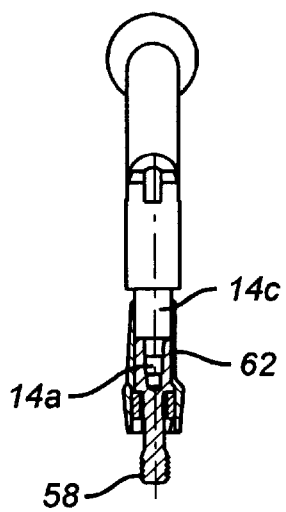 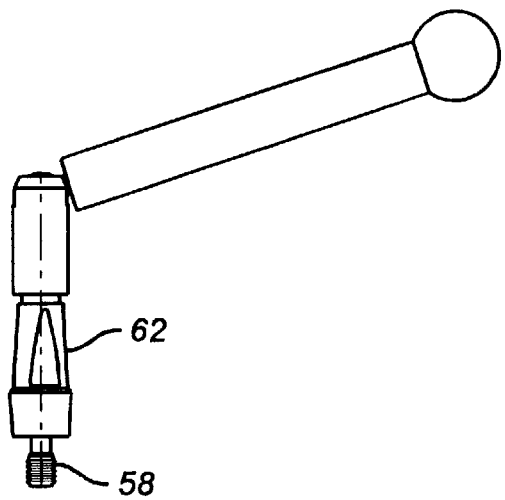
FIG. 14a  FIG. 14b

ABUTMENT DELIVERY SYSTEM

BACKGROUND

The disclosures herein related generally to dental implants and more particularly to a tool for retaining and delivering implant components to a dental implant at an implant site.

The surgical process of dental implant placement includes a bone preparation process including an incision to expose that portion of bone to receive the implant. Progressive drilling and alignment procedures prepare an implant bed in the bone for proper implant sizing and implant placement. The incision is closed and a healing period follows.

When satisfactory healing is confirmed, the top of the implant is exposed and a temporary gingival cuff is attached to the implant for the purpose of contouring the surrounding soft tissue to coincide with the implant components to be subsequently attached to the implant.

There are several concerns related to attaching the implant components. First, space limitations within the month are of concern especially when a single implant is positioned between adjacent natural teeth. These space limitations require tools which are of a suitable size for manipulation in confined spaces. Component retention and delivery to the implant site are critical because the small components are easily dropped, and if dropped in the patient's mouth, can be easily swallowed or aspirated. Because the prosthetic components are often sterilized, and should remain sterile during implantation, a dropped component requires re-sterilization. In addition, the sterile requirements limit the freedom of unprotected manual handling of the components.

Various component delivery techniques have been developed. U.S. Pat. No. 5,105,690 discloses a driver for screws, bolts and the like which have a socket for receiving the bit of a driver, in which a tapered holding section between the bit and the shaft of the drivers serves to hold an article by frictional engagement with the opening edge of the socket when the bit is engaged in the socket for turning the article. The bit is shorter than the depth of the socket, and the holding section expands sufficiently away from the bit so as to make frictional contact with the edge of the socket when the bit is engaged in the socket.

U.S. Pat. No. , 5,690,489 discloses a self-locking cylindrical driver to deliver and assemble internally hexed prosthetic components such as screws and abutments into place. The head of the tool engages and locks with the flat side surfaces of the internally hexed prosthetic component. The tool allows for extra-oral assembly of a component with the tool to minimize any risk of a component falling off or being lost in a patient's mouth during delivery of the component. Final seating of the component is then accomplished using a conventional hexagonal drive tool with appropriate delivery torque. The tool is formed into both a standard hand driven wrench and a contra-angle drill.

U.S. Pat. No. 5,437,550 discloses a tool for affixing a component to a dental implant fixture with a screw passing through the component and threaded into the implant fixture. The tool has two parts telescopically interfitting one within the other, the outer part being tubular for carrying the component at one end, and the inner part fitted at one end for carrying the screw positioned within the component. The component, and the screw within it, can be carried together to the implant fixture where the outer part is used to hold the component in place while the inner part is used to drive the screw into the implant fixture.

A limitation of previous delivery systems is that the various implant components cannot all be delivered and attached by a single versatile tool. Therefore, what is needed is a versatile tool which can engage, retain, deliver and at least initially engage the various components with the implant.

SUMMARY

One embodiment, accordingly, provides such a versatile tool which provides the required retention and delivery features for handling a plurality of implant components. To this end, a tool for retaining and delivering dental implant components includes a retainer member having a delivery end which includes a plurality of concentric, various sized retainer portions.

The principal advantages of the embodiments disclosed herein are that various implant components can be sequentially or simultaneously frictionally engaged by the implant tool for delivery to the implant site. The tool can be immediately removed or used to manipulate the component to cause initial engagement with the implant and then be subsequently removed. A handle may be pivotally attached to the tool if desired by a snap-in, snap-out feature. With the handle detached, an auxiliary drive tool can engage the implant tool for further manipulation of the component into engagement with the implant. The tool enables component removal from sterile packaging for delivery directly to the implant site so as to avoid improper or non-sterile handling. The tool is sized to be smaller than the component being delivered for facilitated access to space limited implant sites.

BRIEF DESCRIPTION OF THE DRAWING FIGURES

FIG. 1a is a side view illustrating an embodiment of a tool for retaining and delivering dental implant components.

FIG. 1b is a cross-sectional view taken along line 1b—1b of FIG. 1a.

FIG. 1c is an end view taken along line 1c—1c of FIG. 1b.

FIG. 2 is an isometric view illustrating another embodiment of the tool attached to a handle.

FIG. 3a is an isometric view illustrating another embodiment of the tool attached to a handle.

FIG. 3b is an end view taken along line 3b—3b of FIG. 3a.

FIG. 4 is an isometric view illustrating another embodiment of the tool attached to a handle.

FIG. 5a is an isometric view illustrating an embodiment of the tool including a ball connected to a socket of a handle.

FIG. 5b is a cross-sectional view taken along line 5b—5b of FIG. 5a.

FIG. 6b is a cross-sectional view taken along the line 6b—6b of FIG. 6a.

FIG. 8a is an isometric view illustrating an embodiment of a hex drive seating tool.

FIG. 8b is an end view taken along line 8b—8b of FIG. 8a.

FIG. 9a is a side view illustrating another embodiment of a tool for retaining and delivering dental implant components.

FIG. 9b is a cross-sectional view taken along line 9b—9b of FIG. 9a.

FIG. 9c is an end view taken along line 9c—9c of FIG. 9b.

FIG. 10a and 10b illustrate an embodiment of the tool and handle connected for delivering a threaded fastener.

FIG. 1a and 11b illustrate an embodiment of the tool and handle connected for delivering a shouldered abutment.

FIG. 12a and 12b illustrate an embodiment of the tool and handle connected for delivering a fixed abutment.

FIG. 13a and 13b illustrate an embodiment of the tool and handle connected for delivering a temporary gingival cuff.

FIG. 14a and 14b illustrate an embodiment of the tool and handle connected for simultaneously delivering a threaded fastener and a fixed abutment.

DETAILED DESCRIPTION

Figure 6A:
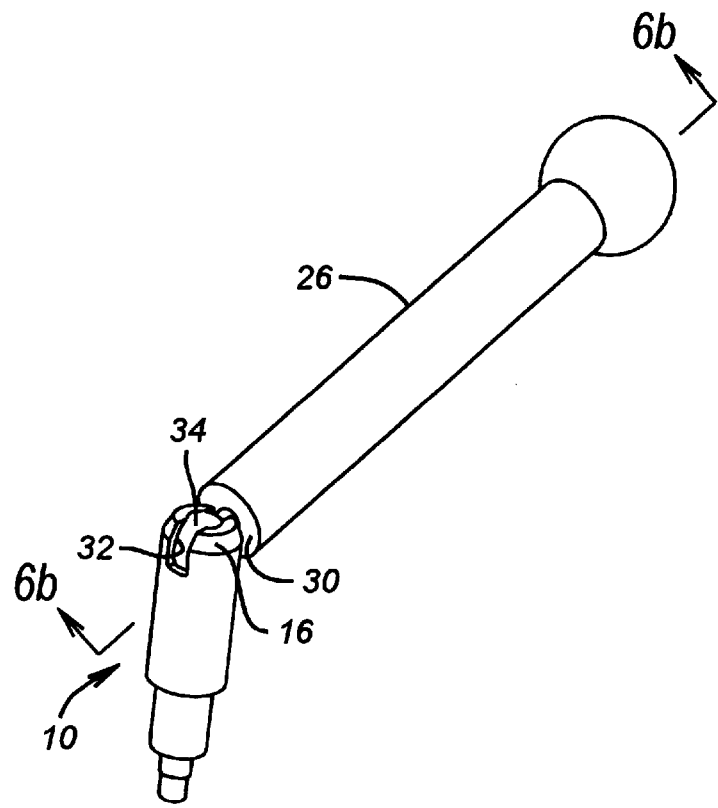
FIG. 6a is an isometric view illustrating an embodiment of the tool including a socket connected to a ball of a handle.

A tool 10, FIGS. 1a, 1b and 1c, is provided for retaining and delivering dental implant components. The tool 10 includes a retainer or post member which has a main body portion 12 and opposite ends 14 and 16. One end is a delivery end 14 and includes a plurality of concentric, various sized portions 14a, 14b and 14c. Each of the portions 14a, 14b and 14c is smaller in cross-section, sequentially, in a direction D1 extending toward the delivery end 14. The entire delivery end 14 may be formed as a tapered member 114, FIG. 2, and portions 114a, 114b and 114c of the tapered member 114 are sized for insertion into various sized dental implant components, to be discussed below. Preferably, the portions 14a, 14b and 14c, FIG. 1a, are formed as stepped down portions, and at least one of the portions 14b is tapered.

The tool 10 is formed of a synthetic resilient, flexible material such as a polymer and may include a split 18, FIGS. 3a and 3b, in at least one of the portions, or may include an irregular surface 20, FIG. 4, including ribs 22, for example. The taper, the steps, the flexible material, the split and the irregular surface all contribute to the delivery end providing a frictional engagement with various dental implant components.

Figure 6B:
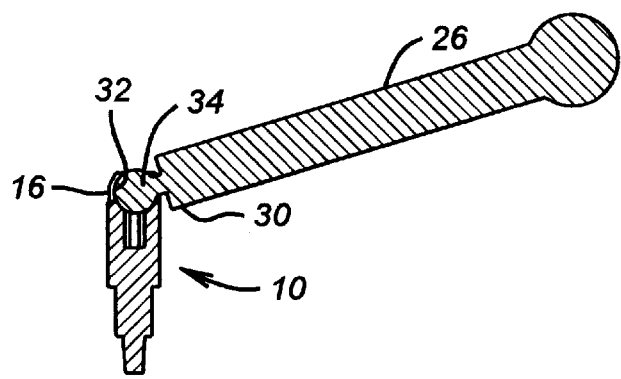
Figure 7A:
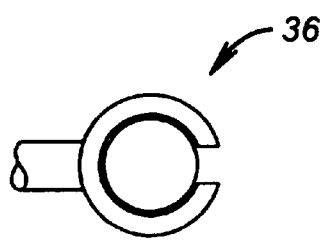
FIG. 7a–7e illustrate embodiments of various connectors for the tool and the handle.
Figure 7B:
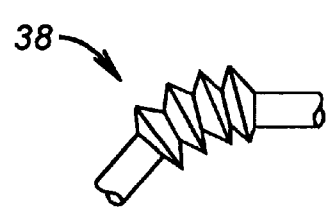
Figure 7C:
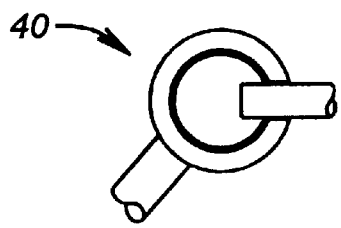
Figure 7D:
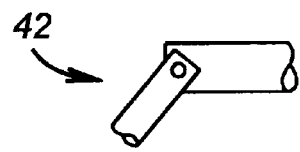
Figure 7E:
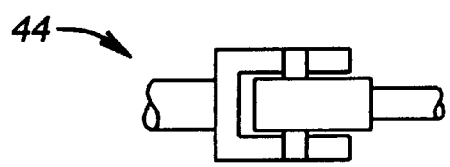

The tool 10, FIGS. 5a and 5b, includes a connector at the other or connection end 16 opposite the delivery end 14. The connector provides for attachment of the tool 10 to an extension member such as a handle 26. This may be accomplished by providing a snap-in, snap-out connection in a quick connect, quick disconnect manner. A preferred type of connection which may be used is a ball and socket connection. This may be accomplished by providing a ball 24 at the connection end 16 of the tool 10 and providing a socket 28 at a connection end 30 of the handle 26. However, a socket 32, FIGS. 6a and 6b, may be provided at the connection end 16 of the tool 10 for engagement with a ball 34 provided at the connection 30 end of the handle 26. Other types of connections for connecting the tool 10 and the handle 26 may include a claw and post connection 36, FIG. 7a, an integrally formed flexible joint 38, FIG. 7b, a hook and eye connection 40, FIG. 7c, a pinned connection 42, FIG. 7d, and a U-joint connection 44, FIG. 7e, each of which provide a movable, flexible, pivotal connection between the tool 10 and the handle 26. Forming the socket 32, FIG. 1b, in the connection end 16 of the tool 10 also permits the additional feature of forming an engagement member 46 or receiver adjacent the socket 32 for receiving a male hex-drive seating tool 48, FIGS. 8a and 8b. The engagement member 46, FIG. 1b, is formed as a female socket having a cross-section formed as a polygon, i.e. hexagonal, FIG. 1c, for receiving the male hex-drive seating tool 48, FIGS. 8a and 8b, having a mating hex cross-section 50 formed on a shaft 52 which extends from a handle 54, provided for turning the shaft 52.

If it is preferred to provide the ball 24, FIGS. 9a, 9b and 9c, on the connection end 16 of the tool 10, a hexagonal socket 56 may be formed in the ball 24 for engagement with the hex-drive seating tool 48.

Various dental implant components may be sequentially fictionally engaged by the various portions of the delivery end of the tool. For example, such components may include a threaded fastener 58, FIGS. 10a and 10b, a shouldered abutment 60, FIGS. 11a and 11b, a fixed abutment 62, FIGS. 12a and 12b, a gingival cuff, 64, FIGS. 13a and 13b and simultaneous engagement of two of the delivery end portions 14c and 14b, FIGS. 14a and 14b, with the fixed abutment 62 and the threaded fastener 58, respectively. In each connection, a portion of the delivery end 14 is inserted into the component or components.

As a result, one embodiment provides a tool for retaining and delivering dental implant components including a retainer member having a delivery end which includes a plurality of concentric, various sized retainer portions.

Another embodiment provides a device for retaining and delivering dental implant components including a post member having a delivery end including a plurality of concentric, various sized portions. Each portion is smaller in cross-section sequentially in a direction extending toward the delivery end. Also, each portion is of a size sufficient for insertion into a receiver in the dental implant component.

Still another embodiment provides a dental implant component retainer and delivery device including a first member having a first end and a second end. A second member is movably connected to the first end of the first member. The second end of the first member includes a plurality of concentric multi-sized portions, each portion being smaller in cross-section in a direction extending toward the second end.

A further embodiment provides a method of retaining and delivering dental implant components. A retainer member is formed having a plurality of concentric multi-sized portions at a terminal end thereof. Various implant components are attached to selected ones of the multi-sized portions. The various components are delivered to a dental implant. The retainer member is removed from the component after delivery.

A still further embodiment provides a device for retaining and delivering implant components including a post member having a multi-sized delivery end. The delivery end includes a plurality of portions of sequentially smaller cross-section for hands-off insertion into, and frictional engagement with, various dental implant components.

As it can be seen, the principal advantages of these embodiments are that various implant components can be sequentially or simultaneously frictionally engaged by the implant tool for delivery to the implant site. The tool can be immediately removed or used to manipulate the component to cause initial engagement with the implant and then be subsequently removed. A handle may be pivotally attached to the tool if desired by a snap-in, snap-out feature. With the handle detached, an auxiliary drive tool can engage the implant tool for further manipulation of the component into engagement with the implant. The tool enables hands-off component removal from sterile packaging for delivery directly to the implant site so as to avoid improper or non-sterile handling. The tool is sized to be smaller than the component being delivered for facilitated access to space limited implant sites.

In the embodiment of FIG. 2, the multiple stepped delivery end of FIG. 1a is replaced by a continuously tapered end.

Similar to the stepped embodiment, the tool retains implant components by means of a friction fit with a receiving feature formed in each implant component. The taper is designed so that the diameters necessary to create a friction fit with different types of implant components, occur at some point along its length. Like the stepped embodiment, this embodiment includes a pivoting handle that removably attaches to the tool and a keyed bore for receiving, for example, the hex drive delivery tool.

In operation, the tapered embodiment is used exactly like the stepped tool. The component is fit on the frictionally engaging portion of the delivery end. The component is then delivered to the implant. The tool can then be immediately removed or first used to manipulate the component to cause initial engagement with the implant and then removed. If insufficient room exists to rotate the tool with the handle attached, the handle can be removed and the delivery end can be manually rotated as a stand-alone unit or by using a second tool such as the hex drive delivery tool.

In the embodiment of FIGS. 3a and 3b, the delivery tool has a split delivery end. When the tool is inserted into the receiving feature of the implant component, the split causes the delivery end to compress. The resilience of the material, coupled with the space provided by the split, then causes the sides of the delivery end to frictionally engage the implant component. Also, when compressed, the geometry of the delivery end becomes tapered allowing the tool to be wedged into the implant component.

In the embodiment of FIG. 4, the delivery tool has ribs that protrude from the stepped delivery portion. The ribs deform when the tool is inserted into the implant component. The addition of ribs may increase the strength of the friction engagement and increase the torque that can be applied before slipping occurs. The ribs on the main body portion of the delivery end, located immediately above the stepped portions, serve to aid in gripping the tool when the delivery end is manually rotated separate from the handle.

Although illustrative embodiments have been shown and described, a wide range of modification change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A tool for retaining and delivering dental implant components comprising:
   a retainer member; and
   a delivery end of the retainer member, the delivery end including a plurality of concentric, various sized retainer portions, wherein at least one of the portions includes a split formed therein for providing a frictional engagement with the implant components.

2. The tool as defined in claim 1 wherein the retainer member is formed of a synthetic material.

3. The tool as defined in claim 1 wherein the retainer member is formed of a flexible material.

4. The tool as defined in claim 1 wherein the portions are smaller in cross-section sequentially in a direction extending toward the delivery end.

5. The tool as defined in claim 1 wherein at least one of the portions includes an irregular surface formed thereon for providing a frictional engagement with the implant components.

6. The tool as defined in claim 1 wherein at least one of the portions is tapered.

7. The tool as defined in claim 1 wherein the retainer member includes a connector for attachment of an extension member at another end opposite the delivery end.

8. The tool as defined in claim 7 wherein the extension member is a handle.

9. A device for retaining and delivering dental implant components comprising:
   a post member having a delivery end and a connector end;
   the delivery end including a plurality of concentric, various sized portions, each portion being smaller in cross-section sequentially in a direction extending toward the delivery end;
   an elongated handle pivotally connected to the connector end of the post member; and
   each portion being of a size sufficient for insertion into a receiver in a dental implant component.

10. The device as defined in claim 9 wherein the post member is formed of a synthetic material.

11. The device as defined in claim 9 wherein the post member is formed of a flexible material.

12. The device as defined in claim 9 wherein at least one of the portions is tapered.

13. The device as defined in claim 9 wherein at least one of the portions includes a split formed therein for providing a frictional engagement with the implant components.

14. The device as defined in claim 9 wherein at least one of the portions includes an irregular surface formed thereon for providing a frictional engagement with the implant components.

15. The device as defined in claim 9 herein the post member includes a connector for attachment of an extension member at another end opposite the delivery end.

16. The device as defined in claim 15 herein the extension member is a handle.

17. A dental implant component retainer and delivery device comprising:
   first member having a first end and a second end;
   a second member movably connected to the first end of the first member, wherein the second member is removably connected to the first end of the first member by a pivotable snap-in, snap-out connection; and
   the second end of the first member including a plurality of concentric, multi-sized portions, each portion being smaller in cross-section sequentially in a direction extending toward the second end.

18. The component retainer as defined in claim 17 wherein the first member is formed of a synthetic material.

19. The component retainer as defined in claim 17 wherein the first member is formed of a flexible material.

20. The component retainer as defined in claim 17 wherein the portions are tapered.

21. The component retainer as defined in claim 17 wherein at least one of the portions includes a split formed therein for providing a frictional engagement with the implant components.

22. The component retainer as defined in claim 17 wherein at least one of the portions includes an irregular surface formed thereon for providing a frictional engagement with the implant components.

23. A method of retaining and delivering dental implant components comprising the steps of:
   forming a retainer member having a plurality of concentric, multi-sized portions at a terminal end thereof;
   snapping a handle into engagement with one end of the retaining member for pivotal connection therewith;

attaching various implant components to selected ones of the multi-sized portions;

delivering the various components to a dental implant; and removing the retainer member from the component.

24. The method as defined in claim 23 wherein the step of attaching various implant components includes the step of sequentially attaching single components.

25. The method as defined in claim 23 wherein the step of attaching various implant components includes the step of simultaneously attaching a plurality of components.

26. The method as defined in claim 23 wherein the step of attaching various components includes the step of inserting at least one of the portions into a receiver in each component for frictional engagement therewith.

27. The method as defined in claim 23 further comprising the step of manipulating the retainer member to initially connect the components to the implant.

28. A device for retaining and delivering dental implant components comprising:

a post member;

a handle pivotally connected to one end of the post member; and a multi-sized delivery end of the post member, the delivery end including a plurality of portions of sequentially smaller cross-section for hands-off insertion into, and frictional engagement with, various dental implant components.

29. The device as defined in claim 28 wherein the post member includes an engagement member for receiving an implant tool, the engagement member being formed in another end opposite the delivery end.

30. The device as defined in claim 29 wherein the engagement member is a female polygon and the implant tool includes a male polygon for engaging the female polygon.

31. The device as defined in claim 28 wherein the post member includes another end opposite the delivery end for receiving a handle member and for receiving an implant tool.

32. A tool for delivering a dental implant component, the tool comprising:

a body having a connector end and a delivery end, the delivery end having a plurality of concentric, various sized retainer portions, the retainer portions adapted to frictionally engage the dental implant component; and a handle pivotally mounted to the connector end of the body.

33. The tool of claim 32 wherein the handle connects to the connector end using a claw and post attachment, a flexible joint attachment, a hook and eye attachment, a pin connection, a ball and socket attachment, or a U-joint attachment.

34. The tool of claim 33 wherein the handle has an elongated cylindrical configuration.

35. The tool of claim 34 wherein the handle is removably connected to the connector end.

* * * * *